United States Patent [19]

Alich et al.

[11] Patent Number: 4,956,885
[45] Date of Patent: Sep. 18, 1990

[54] PATIENT SUPPORT FOR DIAGNOSTIC APPARATUS

[75] Inventors: Thomas Alich, Elmshorn; Peter Flisikowski; Horst Peemoller, both of Hamburg, all of Fed. Rep. of Germany

[73] Assignee: U.S. Philips Corporation, New York, N.Y.

[21] Appl. No.: 410,692

[22] Filed: Sep. 21, 1989

[30] Foreign Application Priority Data

Oct. 3, 1988 [DE] Fed. Rep. of Germany ....... 3833594

[51] Int. Cl.$^5$ .............................................. A61G 7/06
[52] U.S. Cl. ........................................ 5/431; 5/82 R; 378/209
[58] Field of Search ................. 5/82 R, 431; 269/322, 269/328; 378/208, 209

[56] References Cited

U.S. PATENT DOCUMENTS

| | | | |
|---|---|---|---|
| 3,897,345 | 7/1975 | Foster | 378/208 |
| 3,947,686 | 3/1976 | Cooper et al. | 378/209 |
| 4,145,612 | 3/1979 | Cooper | 378/208 |
| 4,262,204 | 4/1981 | Mirabella | 378/209 X |
| 4,566,445 | 1/1986 | Jelsma et al. | 5/82 R X |
| 4,700,938 | 10/1987 | Chambron | 378/209 X |
| 4,805,626 | 2/1989 | DiMassimo et al. | 269/322 X |

FOREIGN PATENT DOCUMENTS

0017454 3/1980 European Pat. Off. .

*Primary Examiner*—Michael F. Trettel
*Attorney, Agent, or Firm*—William Squire

[57] ABSTRACT

The invention relates to a patient support for diagnostic apparatus, notably for an MRI apparatus, comprising a stretcher on which a patient can be arranged so as to be introduced into the diagnostic zone of the apparatus, the support comprising a core of a fiber-reinforced epoxy resin with a coating provided thereon, the core being made of a fiberglass-reinforced synthetic material on an epoxy resin basis with an isotropic fiberglass structure wherethrough cavities extend in the longitudinal direction, which cavities are filled with a fiber glass fleece impregnated with epoxy resin, the upper side being provided with a fiber-reinforced coating on an epoxy resin basis with unidirectional fibers of a synthetic material of a high tensile strength.

6 Claims, 2 Drawing Sheets

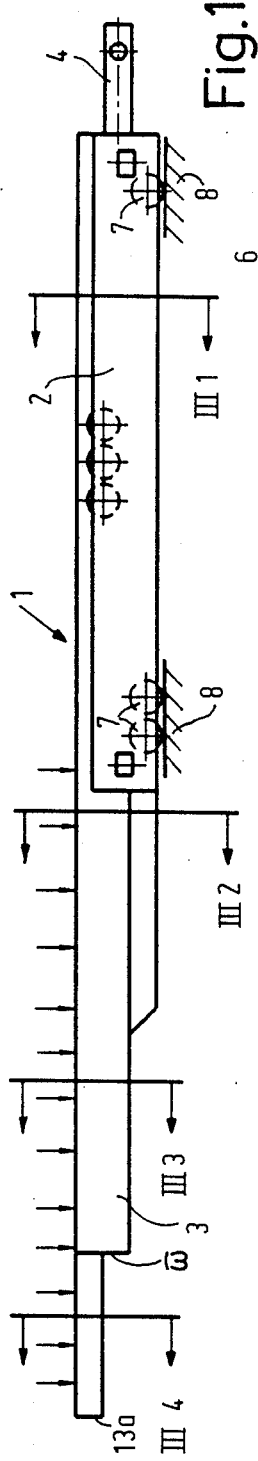
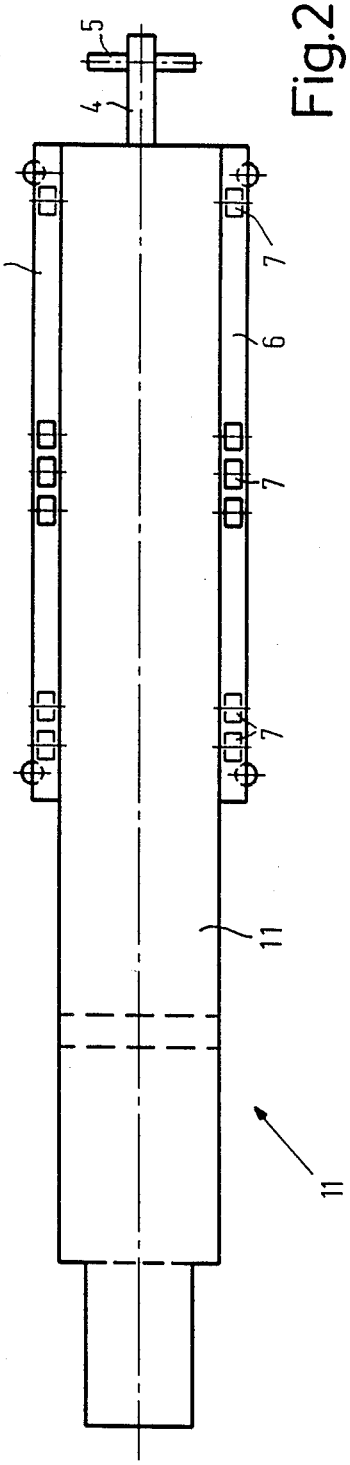
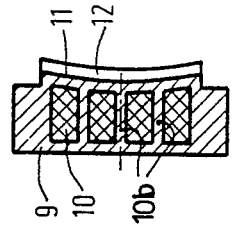
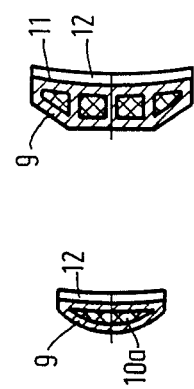
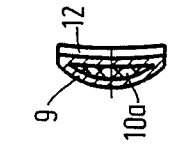

PATIENT SUPPORT FOR DIAGNOSTIC APPARATUS

The invention relates to a patient support for a diagnostic apparatus, notably for an MRI apparatus, comprising a cantilevered stretcher to support an object to be examined and to be introduced into an examination zone of the apparatus, the support comprising a core of fibre-reinforced epoxy resin provided with a coating.

A patient support of this kind which is made of wood and whose surface is covered by a fibre-reinforced polyester resin layer is known from U.S. Pat. Ser. No. 4,145,612. The patient support comprises wheels and can be rolled into the diagnostic zone of the apparatus.

European Patent Application No. 0 017 454 discloses a patient support whose core consists of cured, thermally curable resin containing carbon fibres. The surface coating of this core consists of an epoxy resin impregnated carbon fibre fabric so that it is electrically conductive. This electrical conductivity causes distortions of the magnetic field of an MRI tomography apparatus, i.e. deflection of field lines.

In as far as they are not reinforced the known patient supports exhibit a comparatively high degree of flexure which depends on the patient load. When the patient support is to be used in conjunction with an MRI apparatus, notably high field MRI tomography apparatus, flexure in excess of, for example 4 mm per 2 m is not permissible.

It is an object of the invention to provide a patient support of the kind set forth in which the flexure of a cantilevered stretcher is reduced. Eddy currents are to be precluded so as to avoid deflection of the field lines for use in an MRI apparatus.

This object is achieved in accordance with the invention in that the core is made of a fibreglass-reinforced synthetic material on an epoxy resin basis with an isotropic fibreglass structure wherethrough cavities extend in the longitudinal direction, which cavities are filled with a fibreglass fleece impregnated with epoxy resin, its upper side being provided with a fibre-reinforced coating of a synthetic material on an epoxy resin basis with unidirectional fibres of a synthetic material of high tensile strength.

A patient support of this kind exhibits extremely small flexure of no more than 4 mm over a length of 2 m. The stability of the shape of the patient support is independent of the ambient temperature; moreover, the patient support can be universally used.

In a further embodiment of the invention, the fibreglass-reinforced epoxy resin material of the core includes a fibreglass fabric whose modulus of elasticity amounts to approximately 15,000 N/mm$^2$. Such a material is particularly suitable as a enforcing material for the core.

In a further embodiment of the invention, the unidirectional fibres of the upper coating have a high tensile strength and a modulus of elasticity of approximately 30,000 N/mm$^2$. This fibre material increases the rigidity of the support, against tensile stress.

In a further embodiment in accordance with the invention, the fibreglass fleece impregnated with epoxy resin, being commercially available as "Coromat", has a low density and a high compressive strength of approximately 200 N/mm$^2$ in relation to the low density of approximately 700 kg/m$^3$. This material which fills the cavities reduces the deformation of the core walls in the loaded condition at the expense of only a comparatively small increase of the overall weight of the support.

Finally, in a further embodiment in accordance with the invention perpendicular reinforcement strips of synthetic material such as GFK increase the resistance in the direction of loading.

The invention will be described in detail hereinafter with reference to the drawing. Therein:

FIG. 1 is a side elevation of a patient support in accordance with the invention, FIG. 2 is a plan view of the patient support shown in FIG. 1.

FIG. 3 shows four different sectional views of the patient support, starting with a rear carriage portion and finishing with the front end of the support, the sectional views being denoted as III$_1$, III$_2$, III$_3$ and III$_4$, respectively, in FIG. 1.

Figure 4:
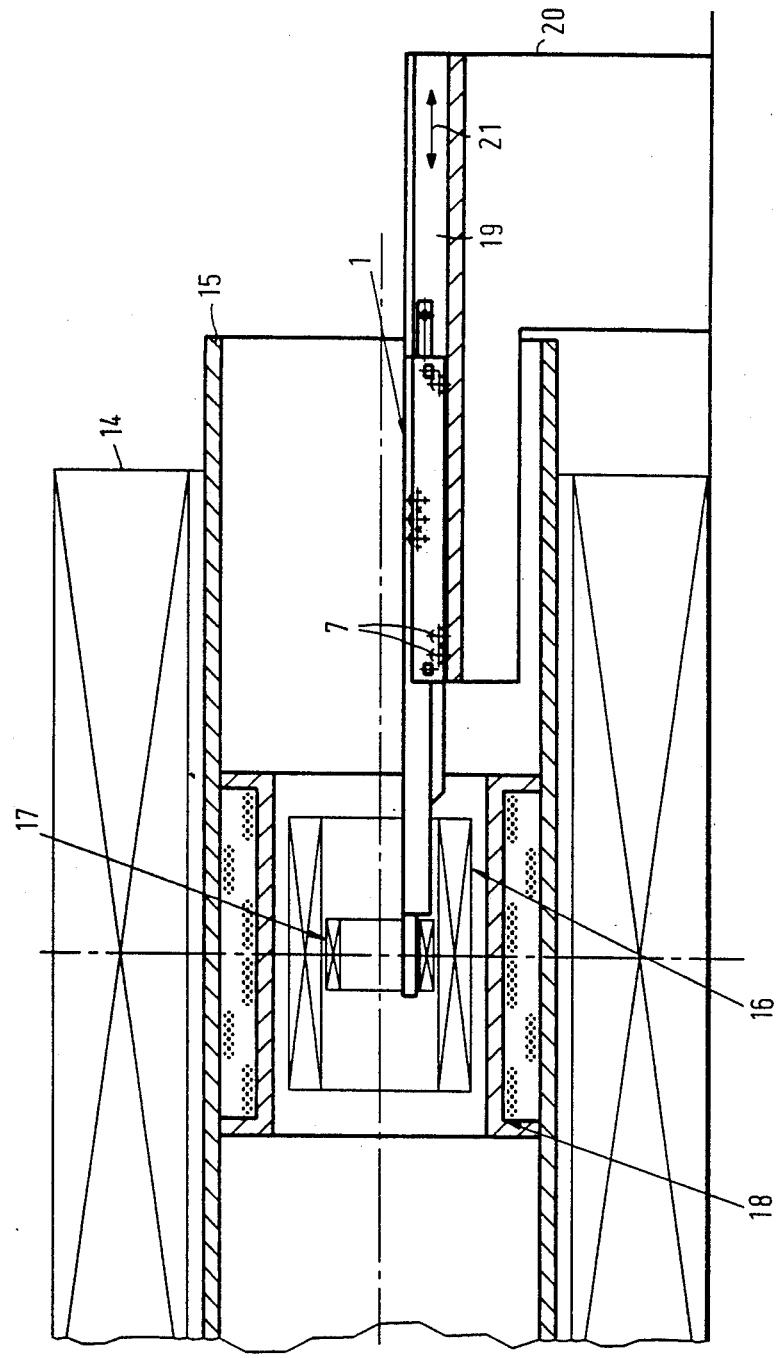
FIG. 4 shows the patient support in conjunction with a 4-T MRI tomography apparatus.

The patient support 1 shown in FIG. 1 comprises a carriage part 2 which supports a cantilevered stretcher 3. The patient support 1 can be displaced by hand, via a grip 4 with a transverse rod 5.

Laterally of the patient support 1 there are provided displacement means 6 which include rollers 7 on which the patient support 1 can be displaced on a surface 8. The arrangement of the displacement means 6 is clearly shown in FIG. 2.

FIGS. 3, 1-3, 4 illustrate the cross-section of the construction of the patient support, using the sectional views III$_1$–III$_4$ of FIG. 1 which are four separate sectional views taken at the area of different cross-sections. The cross-section views of FIG. 3,1 reveals that the patient support is made of three different materials. The core 9 consists of a fibreglass-reinforced synthetic material on the basis of epoxy resin with an isotropic fibre glass structure. Cavities 10 extend in the longitudinal direction in the core 9, which cavities are separated from one another by partitions which also extend in the longitudinal direction.

These cavities 10 are filled with an epoxy resin impregnated fibreglass fleece which is commercially available as "Coromat". This material has a low density in the order of magnitude of 700 kg/m$^3$ and a high compressive strength in the order of magnitude of 200 N/mm$^2$. Because of its low density, it only slightly increases the overall weight of the patient support 1, but substantially reduces the deformation of the support walls in the loaded condition because of its compressive strength.

On the upper side 11 of the patient support there is provided a coating 12 which consists of a fibre-reinforced synthetic material on the basis of epoxy resin. The fibre reinforcement within this coating consists of unidirectional fibres of a synthetic material having a high tensile strength. These fibres are commercially available, for example as "Aramid". These special fibres reinforce and increase the tensile strenght of the patient support exposed to tensile stress.

The sectional views in the FIGS. 3,1 to 3,4 reveal that the cavities 10 are separated from one another by means of vertical partitions 10b which increase the rigidity of the support. The shape of the cavities 10, the partitions 10b and the support changes as the cross-section decreases, but in principle remains the same as far as the front end 13 whereto there is connected a head section 13a. The head section 13a has only one cavity 10a and has a distinctly flatter construction.

FIG. 4 shows how the patient support can be inserted into a 4-T magnet of an MRI apparatus. A supporting tube 15 extends through the 4-T main magnet 14, which tube accommodates either an RF whole-body coil 16 or an RF head coil 17. Between the main magnet 14 and commonly used gradient coils there is arranged a gradient tube 18. No RF shielding is shown; actually, the entire drawing is merely a diagrammatic representation. The patient support 1 is displaced in the directions of a double arrow 21 on a rolling table 19 arranged on a frame 20. Either the head of the patient is introduced into the RF head coil 17 or the entire patient on the stretcher is inserted into the RF whole-body coil.

The flexure of the patient support, being very long because of the 4-T magnet, amounts to less than 4 mm, thus ensuring substantially distortion-free slice images.

We claim:

1. A patient support for a diagnostic apparatus, notably for an MRI apparatus, comprising a cantilevered stretcher to support an object to be examined and to be introduced into an examination zone of the apparatus, the support comprising a core of fibre-reinforced epoxy resin provided with a coating, characterized in that the core is made of a fibreglass-reinforced synthetic material on an epoxy resin basis with an isotropic fibreglass structure wherethrough cavities extend in a longitudinal direction of the stretcher, which cavities are filled with a fibreglass fleece impregnated with epoxy resin, an upper side of the stretcher being provided with a fibre-reinforced coating of a synthetic material on an epoxy resin basis with unidirectional fibres of a synthetic material of high tensile strength.

2. A patient support as claimed in claim 1, characterized in that the fibreglass-reinforced epoxy resin material of the core includes a fibreglass fabric whose modulus of elasticity amounts to approximately 15,000 $N/mm^2$.

3. A patient support as claimed in claim 1, characterized in that the unidirectional fibres of synthetic material of the upper coating have a high tensile strength and modulus of elasticity of approximately 30,000 $N/mm^2$.

4. A patient support as claimed in claim 1, characterized in that the fibreglass fleece impregnated with epoxy resin has a density below about 700 $kg/m^3$ and a compressive strength above about 200 $N/mm^2$.

5. A patient support as claimed in claim 1, characterized in that the cavities are separated from one another in the longitudinal direction by means of vertical partitions which also increase the stretcher rigidity.

6. A patient support as claimed in claim 1, characterized in that the support includes a carriage part which carries the stretcher, the carriage being provided with rolling devices at a pair of longitudinal sides.

* * * * *